(12) United States Patent
Tozzi et al.

(10) Patent No.: US 9,517,132 B2
(45) Date of Patent: Dec. 13, 2016

(54) ACTUATING DEVICE FOR MECHANICAL ADJUSTMENT ELEMENT OF SURGICAL IMPLANT

(75) Inventors: Piergiorgio Tozzi, Lausanne (CH); Alexandre Michalis, Le Grand-Saconnex (CH); Enzo Borghi, Budrio (IT); Daniel Hayoz, Villars-sur-Glâne (CH)

(73) Assignee: Centre Hospitalier Universitaire Vaudois, Lausanne (CH)

( * ) Notice: Subject to any disclaimer, the term of this patent is extended or adjusted under 35 U.S.C. 154(b) by 430 days.

(21) Appl. No.: 14/237,195

(22) PCT Filed: Aug. 2, 2012

(86) PCT No.: PCT/EP2012/065152
§ 371 (c)(1),
(2), (4) Date: Jun. 19, 2014

(87) PCT Pub. No.: WO2013/020889
PCT Pub. Date: Feb. 14, 2013

(65) Prior Publication Data
US 2014/0350664 A1    Nov. 27, 2014

(30) Foreign Application Priority Data
Aug. 5, 2011  (EP) .................................. 11176761

(51) Int. Cl.
*A61F 2/24*       (2006.01)
*A61B 17/12*    (2006.01)
(Continued)

(52) U.S. Cl.
CPC ....... *A61F 2/2466* (2013.01); *A61B 17/12013* (2013.01); *A61F 2/2442* (2013.01);
(Continued)

(58) Field of Classification Search
CPC ............ A61F 2/2448; A61F 2250/0004; A61F 2/2442; A61F 2/2445; A61F 2/2466; A61F 5/0066; A61B 17/12013; A61B 2017/00398
(Continued)

(56) References Cited

U.S. PATENT DOCUMENTS

| 5,064,431 A | 11/1991 | Gilbertson et al. |
| 7,713,298 B2 | 5/2010 | Shaoulian et al. |
| 2008/0097487 A1* | 4/2008 | Pool ........................ A61F 5/003 606/151 |

FOREIGN PATENT DOCUMENTS

| EP | 1736123 | 12/2006 |
| WO | 01/45486 | 6/2001 |

(Continued)

*Primary Examiner* — Katherine M Shi
(74) *Attorney, Agent, or Firm* — Davis & Bujold PLLC; Michael J. Bujold (57) ABSTRACT

The present invention concerns an actuating device for actuating a mechanical adjustment element of surgical implant, said mechanical adjustment element allowing to modify the functional shape and/or the functional size of the surgical implant when actuated, said actuating device comprising transmission means linked with one end to the mechanical adjustment element and able to move the mechanical adjustment element when said transmission means are actuated, connecting means (7) mounted on the other end of the transmission means and able to actuate the transmission means, said connecting means (7) comprising coupling means and driving means (24) comprising complementary shaped coupling means, said driving means (24) being designed to be removable and fitted into the coupling means for moving the mechanical adjustment element by driving into movement a movable part of the connecting means (7).

13 Claims, 7 Drawing Sheets

(51) Int. Cl.
*A61F 5/00* (2006.01)
*A61B 17/00* (2006.01)
(52) U.S. Cl.
CPC .......... *A61F 2/2448* (2013.01); *A61F 5/0056* (2013.01); *A61F 5/0066* (2013.01); *A61B 2017/0042* (2013.01); *A61B 2017/0046* (2013.01); *A61B 2017/00212* (2013.01); *A61B 2017/00398* (2013.01); *A61B 2017/00539* (2013.01); *A61B 2017/00734* (2013.01); *A61F 2250/001* (2013.01)
(58) Field of Classification Search
USPC ................ 606/2.11, 2.37; 623/140; 600/37
See application file for complete search history.

(56) References Cited

FOREIGN PATENT DOCUMENTS

| | | |
|---|---|---|
| WO | 2008/097999 | 8/2008 |
| WO | 2010/014671 | 2/2010 |
| WO | 2011/011443 | 1/2011 |

\* cited by examiner

Fig. 12a

ACTUATING DEVICE FOR MECHANICAL ADJUSTMENT ELEMENT OF SURGICAL IMPLANT

TECHNICAL FIELD

The present invention relates to the technical field of surgical implants which have to be adjusted when placed in a patient's body. Such implants are already used in different medical applications.

Such a surgical implant can be for instance an annuloplasty ring for repairing atrioventricular cardiac valves (such as mitral valve and tricuspid valve) to prevent backflow from the ventricles into the atrium during systole. In the interest of simplicity, the description of the invention is mainly focused on mitral valve, but the concept, the function and the benefit apply to tricuspid valve also.

Other medical applications may also enter within the scope of the present invention.

The present invention concerns more particularly an actuating device for actuating the surgical implants, resulting, for instance in a modification of a shape and/or a size of at least a part of the surgical implant.

The present invention concerns also surgical implants comprising such an actuating device.

BACKGROUND OF THE INVENTION

In the application concerning the repairing of atrioventricular cardiac valves, mitral annuloplasty relays on the implant of mitral ring having fixed shape and size. During the classical mitral valve repair procedure, the surgeon sizes the mitral annulus and chooses the mitral ring accordingly. This procedure is done on the arrested heart under cardiopulmonary bypass, which is not a physiologic condition. It is only after the weaning off the cardiopulmonary bypass that it is possible to assess the quality of the mitral repair. In other words, the surgeon has to wake up the patient to verify if he succeeded in the mitral repair. If the repair fails, the patient undergoes a second surgical operation. Surgeons and cardiologists express a need in the possibility to adjust the ring after implantation. Having a mitral ring that changes its size after implantation and on a beating heart, could improve the quality of the mitral repair and overcome the annulus miss-sizing problem.

Some solutions have been found to reduce the risk of ineffective mitral annuloplasty.

U.S. Pat. No. 7,713,298 discloses an annuloplasty ring which comprises shape memory members configured to transform said annuloplasty ring from a first configuration having a first size of a ring dimension to other configurations having a size of the ring dimension, which is less than said first size. One of the drawbacks of such shape memory members is that they are responsive of changes in temperature and/or exposure to a magnetic field.

U.S. Pat. No. 5,064,431 discloses an adjustable annuloplasty ring for an orifice, comprising: a flexible fabric tube formed in the shape of a ring, means for dividing the tube into an inner channel and an outer channel which functions as a sewing flange by which the ring may be sutured to tissue surrounding the orifice, at least two drawstrings for adjusting the size and shape of the ring disposed in the inner channel, the drawstrings extending substantially around the circumference of the ring and having ends protruding from openings in the tube, each drawstring being coupled to the tube at least two separate anchor points. The size and shape of the ring may be adjusted by selectively tightening one or more ends of the drawstrings to constrict portions of the ring.

However, a main drawback of such mitral rings is that their size can be adjusted only one time after implantation.

Another drawback is that the change in ring's shape concerns the entire ring, not a part of it, therefore inducing great reduction in atrio-ventricular valve orifice area. This reduction could generate a clinical problem known as valve stenosis. Another drawback is that the change in shape is irreversible, therefore, if the ring is too tight, it could generate valve stenosis that would eventually deserve major heart surgery to be corrected.

WO 2011/011443 describes an annuloplasty ring assembly comprising a mechanical adjustment element which allows to modify a functional shape and/or size of a ring when actuated. The assembly comprises also transmission means linked with one end to the mechanical adjustment element. The assembly comprises also connecting means mounted on the other end of the transmission means, said connecting means comprising coupling means and driving means with complementary shaped coupling means. The driving means are designed to be removable and fitted into the coupling means for modifying the size/shape of the ring with the help of the driving means.

However, this document does not disclose a mechanical adjustment element which is able to move when the transmission means are actuated. This document discloses specifically a shape memory material which changes its size in response to a provided energy. In this document, the connecting means are not able to actuate the transmission means. Indeed, the transmission means are used only for an energy transmission. Additionally, the driving means are not designed for moving the mechanical adjustment element by driving into movement a movable part of the connecting means but merely to ensure an electrical connection for the energy transmission to the shape memory material.

EP 1 736 123 describes a bi-directional communication system for use with a restrictive opening device such as a gastric ring or band implanted within a patient. The device comprises means for a mechanical adjustment of the opening device which allows modifying a functional size of the ring when actuated. The system comprises also transmission means linked with one end to the opening device. The assembly comprises also connecting means mounted on the other end of the transmission means, said connecting means comprising coupling means and driving means designed to be removable and fitted into the coupling means for modifying the size of the ring. The driving means comprises for instance injection means associated to an injection port for the injection of a liquid which inflates the ring or band.

However, this document does not disclose a mechanical adjustment element which is able to move when the transmission means are actuated. This document discloses specifically a band or opening device which changes its size in response to a driving signal that inflates the band. In this document, the connecting means are not able to actuate the transmission means. Indeed, the transmission means are used only for a transmission of a liquid into the band. Additionally, the driving means are not designed for moving the mechanical adjustment element by driving into movement a movable part of the connecting means but merely to ensure that a liquid is transmitted to the band.

WO 2010/014671 describes a system for adjusting the dimensions of an adjustable implant such as a mitral valve ring in a patient's body. The system comprises an annuloplasty ring assembly comprising a mechanical adjustment element which allows to modify a functional shape and/or size of a ring when actuated. More specifically, the system comprises an adjustable ring associated with drawstrings. When the drawstrings are tensioned, the ring is deformed. However, when the drawings are tensioned, a large zone of the ring is deformed. It is not possible to deform a precise part of the ring.

WO 01/45486 relates to an urinary incontinence treatment apparatus. This document describes a ring assembly comprising a mechanical adjustment element which allows to modify a functional shape and/or size of a ring when actuated. The assembly comprises also transmission means linked with one end to the mechanical adjustment element. The assembly comprises also connecting means mounted on the other end of the transmission means, said connecting means comprising coupling means and driving means such as an electrical motor.

The described apparatus however does not comprise driving means that are designed to be removable and fitted into the coupling means for modifying the size/shape of the ring. And more precisely, the connecting means and the driving means do not comprise complementary shaped coupling means with removable cooperation for actuating the adjustment element.

Therefore there are, at the present time, no adequate solutions, whether commercial or in the literature, for a mitral ring having a size which can be changed and adjusted several times, on a regular basis, after implantation and on a beating heart.

Additionally, there are at the present time, no adequate solutions, whether commercial or in the literature, for an actuating device which provides a reliable and non definitive shape of an annuloplasty ring and which can be operated very easily.

More generally, there are at the present time, no adequate solutions, whether commercial or in the literature, for an actuating device which provides a reliable adjusting of a surgical implant which is adapted for different medical applications and which can be operated very easily.

Moreover, the known actuating devices need in the most of the cases, technically complicated driving means which increase substantially the costs of these actuating devices. By the way, there is no assurance that such driving devices will remain reliable after being housed in a human's body for a long period of time.

OBJECTS AND SUMMARY OF THE INVENTION

Consequently, an object of the present invention is to propose a novel actuating device for a surgical implant which does not present the above-mentioned drawbacks and that is particularly reliable.

Another object of the present invention is to propose a novel actuating device for surgical implant which is simple to handle at any time after its implantation in the patient's body.

Another object of the present invention is to propose a novel actuating device for a surgical implant which provides a precise and reliable position of a localized particular shape or a localized specific size, designed to enhance the function of the surgical implant.

Another object of the present invention is to propose a novel actuating device for surgical implant which diminishes substantially the size of the parts which have to be kept into the patient's body.

Another object of the present invention is to propose a novel actuating device for surgical implants that requires low invasive surgical procedure to accomplish the actuating function.

The objects given to the invention are achieved with the help of an actuating device for actuating a mechanical adjustment element of a surgical implant, said mechanical adjustment element allowing to modify the functional shape and/or the functional size of the surgical implant when actuated, said actuating device comprising transmission means linked with one end to the mechanical adjustment element and able to move the mechanical adjustment element when said transmission means are actuated, connecting means mounted on the other end of the transmission means and able to actuate the transmission means, said connecting means comprising coupling means, and driving means comprising complementary shaped coupling means, said driving means being designed to be removable and fitted into the coupling means for moving the mechanical adjustment element by driving into movement a movable part of the connecting means.

A functional shape and a functional size of a surgical implant are defined as a shape and a size can influence the functioning of an organ in which or on which the surgical implant is placed.

In an embodiment in accordance with the invention, the transmission means comprise at least one cable linking the mechanical adjustment element to the connecting means.

In an embodiment in accordance with the invention, the connecting means comprise a housing frame which includes a pulley for winding up and/or unwinding the cable and setting into movement the mechanical adjustment element when said pulley is driven into rotation.

In an embodiment in accordance with the invention, the movable part comprises a rotating connecting element which is mounted on the housing frame and which is fixed to the pulley and which turns with the pulley.

In an embodiment in accordance with the invention, the coupling means are designed to set into rotation the rotating connecting element with respect of the housing frame.

In an embodiment in accordance with the invention, the coupling means comprise a polygonal shaped connecting hole in the center of the rotating connecting element and at least two additional connecting holes in the housing frame on opposite locations with respect of the polygonal shaped connecting hole, said complementary shaped coupling means comprising a polygonal shaped connecting pin and two additional connecting pins on opposite locations with respect of the polygonal shaped connecting pin, said driving means being designed to set into a relative rotation the polygonal shaped connecting pin and additional connecting pins.

In an embodiment in accordance with the invention, the additional holes and the additional pins may also have a polygonal shape.

In an embodiment in accordance with the invention, the rotating connecting element presents an opened access on its top and a conical shaped gap with a bottom in which is machined the polygonal hole.

In an embodiment in accordance with the invention, the bottom comprises a magnetic material. The association of the conical shaped gap with the magnetic bottom enhances the coupling with the driving means.

In an embodiment in accordance with the invention, the conical shaped gap may be filled with a malleable gel. The additional connecting holes may also be covered with the malleable gel.

Advantageously, the housing frame comprises a peripheral wall surrounding the polygonal connecting hole and the additional connecting holes, for delineating a space which may be filled with the malleable gel.

In another embodiment in accordance with the invention, the external surface of the connecting means is covered with a self-sealing silicon or polymeric element, such as a foil or layer, in order to prevent direct contact between human tissue and the actuating device. This external protection allows however, the passage of the polygonal shaped pin and of the additional pins.

In an embodiment in accordance with the invention, the housing frame comprises attaching holes, which may be used to attach the connecting means to the patient's rips.

In an embodiment in accordance with the invention, the driving means are designed to be manually activated and comprise a substantially cylindrical hollow tool part presenting an annular edge on which the additional pins are protruding and an actuating part which is sliding and rotating in the hollow tool part and which has a crossing end comprising the polygonal shaped pin, said crossing end being protruding from the annular edge.

In another embodiment in accordance with the invention, the driving means comprise a removable control unit/actuator attached to the housing frame and subcutaneous electrical contacts connected to the control unit/actuator, said electrical contacts being designed for providing a connection to a source of energy.

In an embodiment in accordance with the invention, the control unit/actuator comprises an electric motor, said complementary shaped coupling means comprising a motor head on which the polygonal shaped pin is attached to the rotor of the electric motor and the additional pins are attached to the stator of the electric motor.

In an embodiment in accordance with the invention, the actuation device is designed to allow a bidirectional movement of the mechanical adjustment element.

In an embodiment in accordance with the invention, the actuation device is designed to allow a reversible movement of the mechanical adjustment element.

The present invention relates for example to an actuating device applied to a surgical implant that is an annuloplasty ring for repairing an atrioventricular cardiac valve, said mechanical adjustment element being a sliding pushing element.

Such an annuloplasty ring comprises an external support ring, an inner adjustable ring, the sliding pushing element being mounted between external and inner rings, said pushing element being designed to slide, when actuated, along the external ring while pushing the inner ring locally in such a way that a precise part of the inner ring id deformed without modifying the perimeter of said inner ring.

An advantage of the actuating device in accordance with the invention is that it comprises a manually operated solution which is precise enough to enhance the functioning of a cardiac valve. Once the best position is found, the particular shape of the inner ring is not affected over very long period of time.

The present invention relates for example to an actuating device applied to a surgical implant that is a gastric band placed around a stomach, said mechanical adjustment element being able to modify the diameter of the gastric band, resulting in a local tightening of the stomach.

The present invention relates for example to an actuating device applied to a surgical implant that is an artery band placed around a pulmonary artery, said mechanical adjustment element being able to reduce the diameter of the artery band, resulting in a tightening of the pulmonary artery.

The invention relates for example to an actuating device applied to a surgical implant that is an artificial sphincter (urinary and/or fecal). Said mechanical adjustment element being able to reduce the diameter of the conduit (urethra and/or intestine), resulting in controlling the flow through the said conduit.

The objects given to the invention are also achieved with the help of a surgical implant comprising a mechanical adjustment element, said mechanical adjustment element being able to modify a functional shape and/or a functional size of the surgical implant when actuated, said surgical device comprising an actuating device as described above.

An advantage of the actuating device in accordance with the invention lies in the fact that it is very easy to handle for adjusting the shape or the size of a surgical implant which is housed in a human body.

Another advantage of the actuating device in accordance with the invention lies in that the parts of the actuating device which remain in the patient's body are not cumbersome.

Another advantage of the actuating device in accordance with the invention lies in that it can be adapted very easily to different medical applications.

The parts of the actuating device in accordance with the invention are also inexpensive.

Another advantage is that the actuating device according to the invention, requires low invasive surgery, that is as less invasive as an intramuscular injection for its actuation.

BRIEF DESCRIPTION OF THE DRAWINGS

The invention and its advantages also appear in greater detail from the following description of an embodiment given by way of illustration and with reference to the accompanying figures in which.

DETAILED DESCRIPTION

Elements that are structurally and functionally identical, and that are present in more than one distinct figure or illustration, are given the same numeric or alphanumeric reference in each of them.

The present invention described below relates more particularly to an annuloplasty ring especially for repairing regurgitating atrioventricular cardiac valves, such as mitral valve and tricuspid valve. The scope of the invention is however not limited with this particular application. The present invention concerns also many other medical/surgical applications.

FIGS. 1a, 1b, 2 and 3 show an annuloplasty ring 1 comprising an external support ring 2, an inner adjustable ring 4 and a mechanical adjustment element. The mechanical adjustment element is a pushing element 6 designed to slide between the external support ring 2 and the inner adjustable ring 4 by using the external ring 2 as a support to push or press on the inner ring 4, in such a way that a precise part of the inner ring is deformed without modifying the perimeter of the inner ring.

The actuating device is designed to control said pushing element 6.

Advantageously, the external ring 2 is rigid and not adjustable. Preferably, it may be made of rigid biocompatible material like a metallic material, as steel, gold or titanium, or polyether ether ketone (PEEK).

The external ring 2 is not fixed to the mitral annulus and only provides the support for the adjustment of the inner ring 4. This allows an extremely precise reshaping of the ring any time after its implant.

Advantageously, the external ring 2 may comprise an inner flange comprising a first part 10 on which the pushing element 6 is able to slide and a second part 12 to which the facing part of the inner ring 4 is fixed. Preferably, the external ring 2 may substantially have a D shape comprising a linear side corresponding to the second part 12 and a convex side corresponding to the first part 10.

Figure 2:
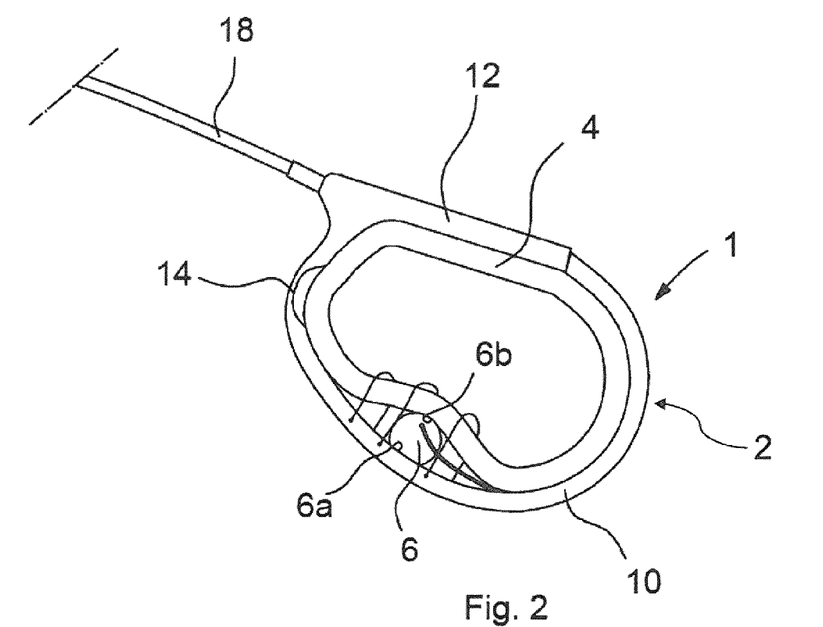
FIG. 2 is a detailed view of the ring of FIG. 1, the pushing element of the annuloplasty ring of FIG. 1 being in a first position.
Figure 3:
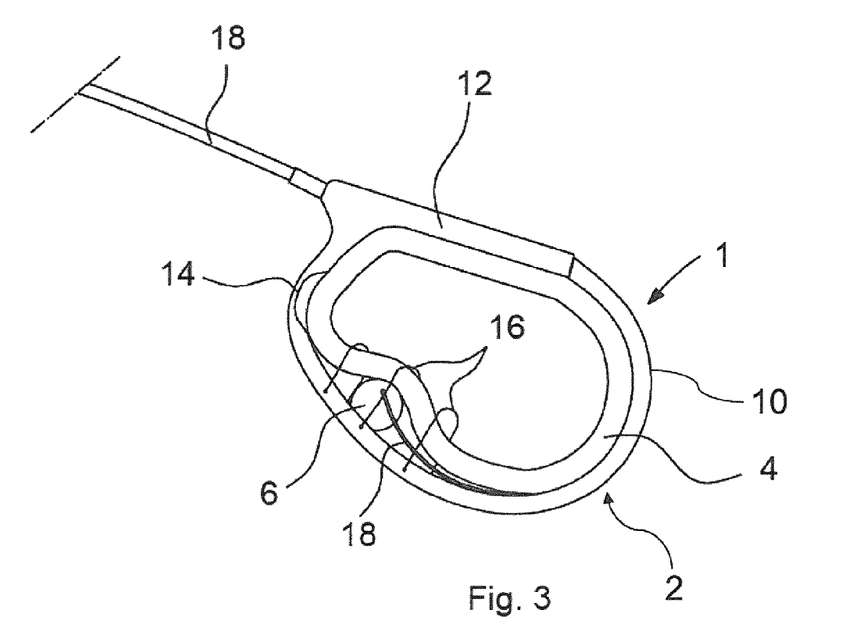
FIG. 3 is another detailed view of the ring of FIG. 1, the pushing element of the annuloplasty ring of FIG. 1 being in a second position.

Advantageously, the inner flange of the external ring 2 may comprise a recess 14 in which the pushing element 6 can be received, partially or completely, when it is in an initial position.

The inner ring 4 is preferably made of a flexible material, as biocompatible polymers, or may be a ring with a spring core.

The inner ring 4 is designed to be fixed to the mitral annulus using standard surgical technique.

The inner ring 4 comprises a linear part which is fixed to the linear part of the external ring 2 by any means known by one skilled in the art, as bonding or welding.

Several arches 16 may be mounted on the external ring 2 and around the inner ring 4 to avoid the overlapping of the two rings. The connection between each arch 16 and the external ring 2 allows the arch 16 to pivot or rotate with respect to the external ring 2 in such a way that the apex of the arch 16 always touches the inner ring 4.

Between the external ring 2 and the inner ring 4 is placed the pushing element 6. Advantageously, said pushing element 6 has a height greater than the distance between the external ring 2 and the inner ring 4 when it is not deformed in such a way that the pushing element 6 is still on contact with the external ring 2 and the inner ring 4. When the pushing element 6 is actuated and slides between said external and inner rings 2 and 4, it leans against the external rigid ring 2 and uses such external rigid ring 2 as a support to push, and more specifically to press on the inner flexible ring 4, and deform of precise part of said inner ring 4.

Advantageously, the pushing element 6 comprises a first surface 6a able to slide on the inner flange of the external ring 2 and a second surface 6b able to slide on the inner ring 4 and to push and press on it.

The pushing element 6 is activated by the actuating device. In a preferred embodiment, said actuating device comprises transmission means linked to the pushing element 6 and able to move the pushing element 6 when said actuating device is actuated.

In some embodiments, the transmission means may be mechanical, by using a cable 18 or hydraulic by using any fluid which is able to transmit to the pushing element 6 a sliding movement.

Preferably, the transmission means may comprise at least one braided cable 18 linked to the pushing element 6. One end of the cable 18 is placed between the inner flange of the external ring 2 and the inner ring 4 and is connected to the pushing element 6.

Cable 18 is protected by a coaxial sheath and slides in the coaxial sheath to transfer the relative movement. The sheath can be made for example of polyimide, PTFE composites (PTFE and fluoroethylkene polymers), pure PTFE, or other appropriate biocompatible polymers. Cables are well known in surgery. The cables can be made for example out of polyamide like Nylon®, polyether block amide, PTFE, or other appropriate polymers. Alternatively, other materials, as stainless steel or titanium, can be used. Surgeon is used to place cables in the human body.

Figure 1A:
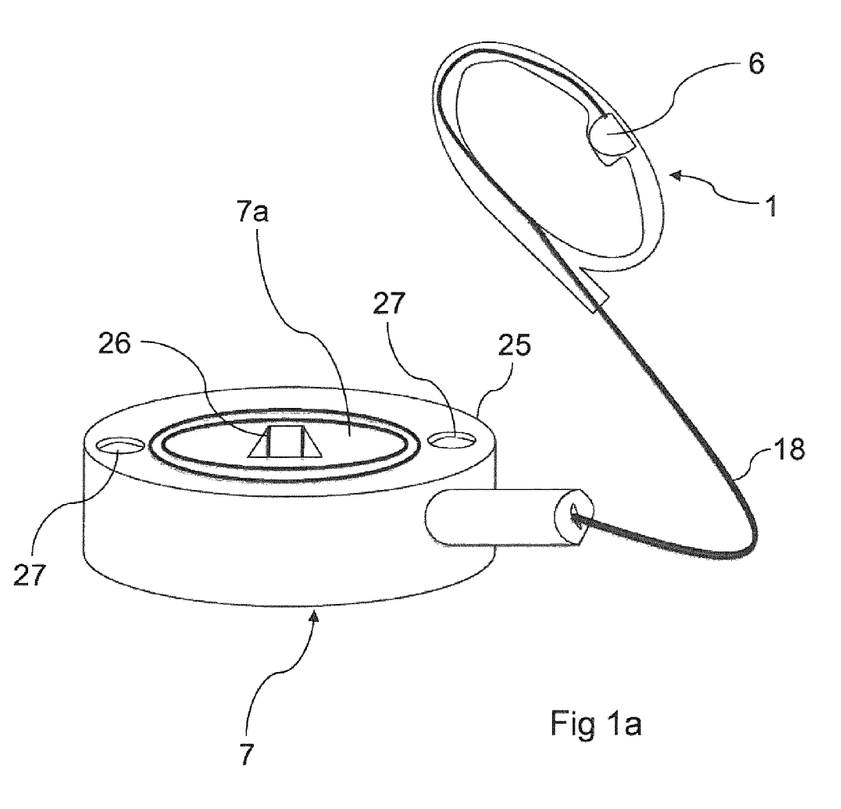
FIG. 1a is a schematic view of an embodiment of an annuloplasty ring connected to an actuating device according to the present invention.
Figure 1B:
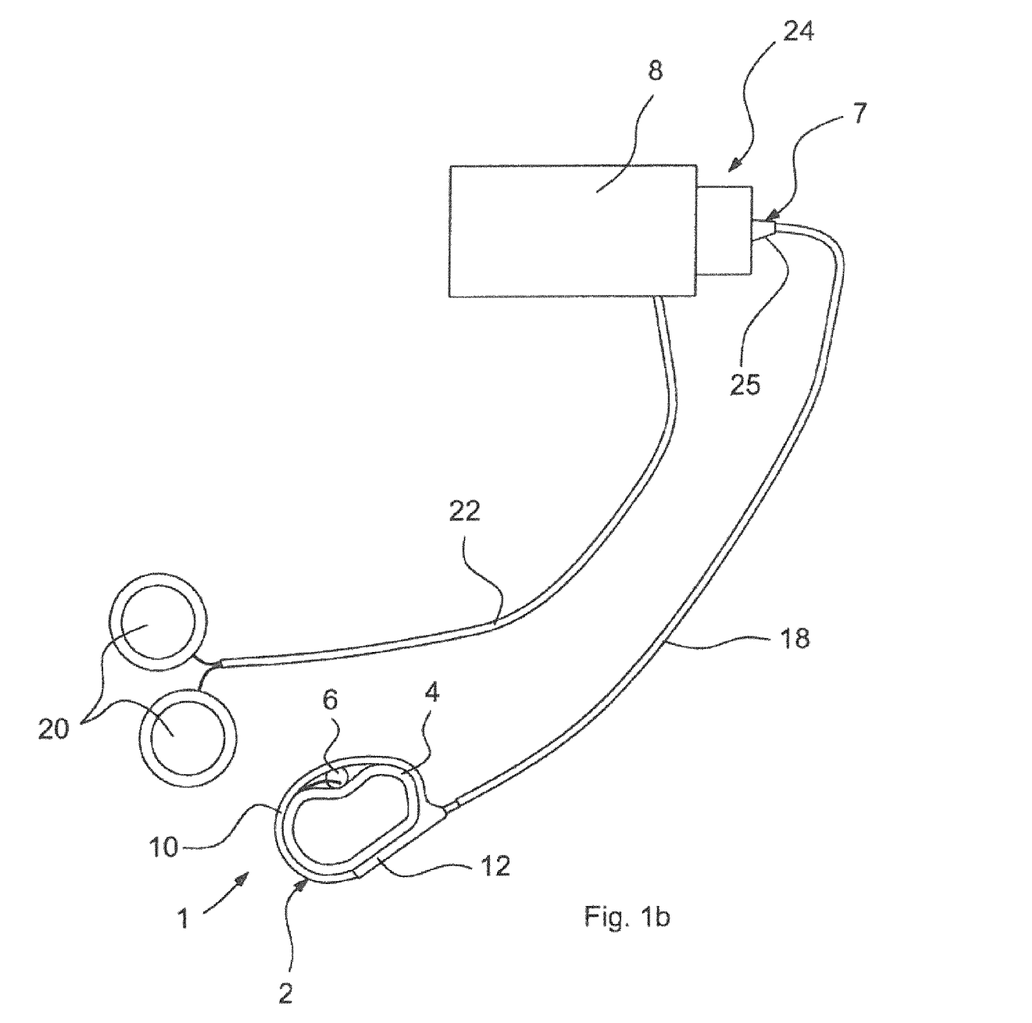
FIG. 1b is a schematic view of an embodiment of an annuloplasty ring connected to another embodiment of an actuating device according to the present invention.

In the embodiment as shown on FIG. 1b, such an actuating device may further comprise by way of example, an actuator and its control unit 8.

The actuating device is designed to provide the force needed to produce the sliding of the pushing element 6 and the corresponding deformation of the inner ring 4. The actuator/control unit 8 may comprise an electric motor.

Preferably, the control unit and the actuator 8 are placed away from the external and inner rings 2 and 4, for example in a box in the subcutaneous tissue.

The annuloplasty ring 1 further comprises a source of energy for the control unit. Said source of energy can be implantable or placed outside the body of the patient. An implantable source of energy may be a transcutaneously rechargeable battery. Such battery is for example a Lithium-Ion or Lithium Polymer rechargeable battery commercialized by GreatBatch and others.

In other embodiments, the source of energy may comprise subcutaneous electrical contacts 20 which are linked to the control unit by electrical wires 22. Such electrical contacts 20 are placed under the skin of the patient and energy is supplied from an external source of energy to the control unit via said electrical contacts 20, when needed.

Advantageously, the control unit may be controlled via a remote control unit using for example a telemetric coupling system, said remote control unit being placed outside the patient body.

In the simplest embodiment of the invention, the actuating device may be designed to be manually activated. For example, the actuating device may comprise a manually activated screw like system connected to the cable 18, in such a way that the pushing element 6 moves, via the cable 18, when said system is manually actuated.

In a more complex embodiment, the cable 18 is moved by using an electric engine or a hydraulic mean positioned outside the patient's body.

Advantageously, the actuating device may be designed to allow a bidirectional movement of the pushing element 6.

In some embodiments comprising an actuator 8, the actuating device may comprise a second cable 18 placed between the inner flange of the external ring 2 and the inner ring 4, on the side opposite to the side on which the first cable 18 is placed. The second cable 18 is linked to the opposite side of the pushing element 6 and linked to a second actuator 8 and to a second control unit or to the same control unit, in such a way that the first cable moves the pushing element in one direction and the second cable 18 moves the pushing element 6 in the opposite direction. A third subcutaneous electrical contact may be provided to supply energy to the second control unit.

Figure 12:
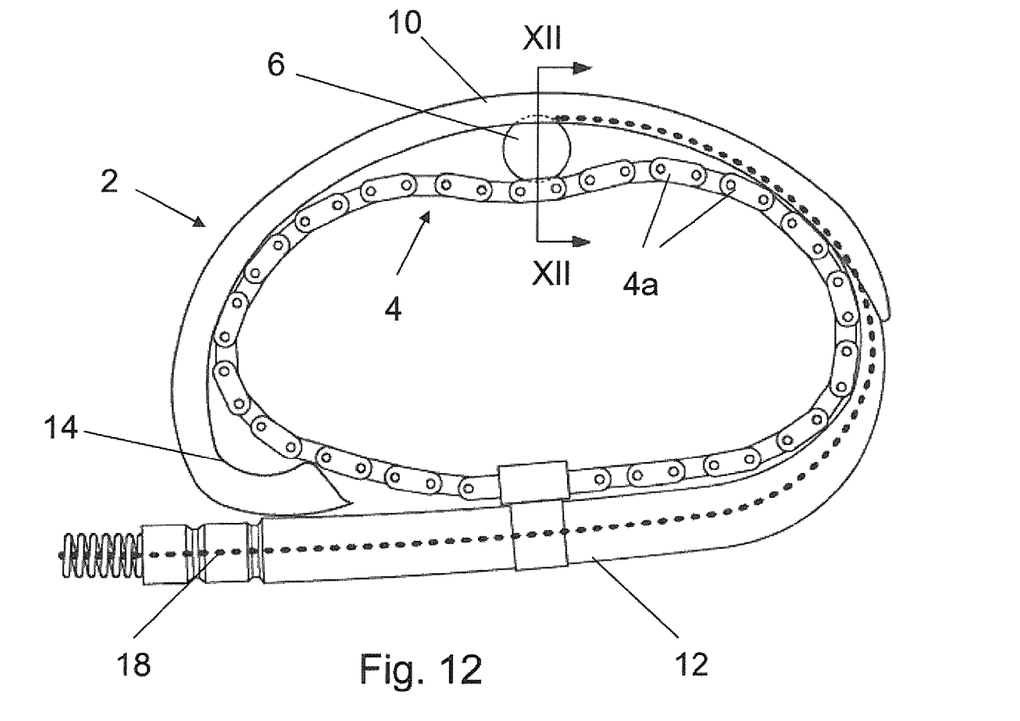
FIGS. 12 and 12a are respectively a view and a cross-sectional view of another embodiment of the annuloplasty ring used in the present invention.
Figure 12A:
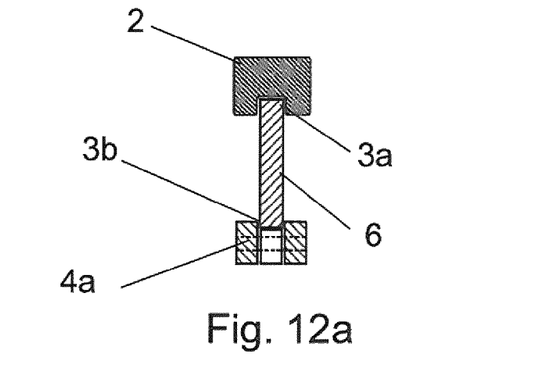

In other embodiments comprising an actuating device which is manually activated, the pushing element 6 is connected on each side to a cable 18. The two cables 18 run parallel to the external ring 2 and are connected to its actuator system. Pulling one cable 18 at a time results in pushing element displacement backward and/or forward. The two cables 18 are for instance partly winded up on their respective pulley or on a same pulley. FIGS. 12 and 12a show another embodiment of the annuloplasty ring system of the invention. FIG. 12a is a cross-sectional view along XII-XII of FIG. 12.

In this embodiment, the inner ring 4 is a chain comprising links 4a which are articulated ones with respect to the others, in such a way that the chain is flexible. As the links 4a are articulated ones with respect to the others, this embodiment allows that a precise part of the inner ring 4 is deformed without deforming the other part of the inner ring.

Moreover, the external ring 2 and the chain comprise facing channels or grooves 3a, 3b in which the pushing element 6 slides, in such a way the pushing element is maintained between the external and the inner rings 2 and 4. Obviously, one skilled in the art can use in another embodiment a pushing element which comprises two lateral grooves able to receive a slide bar provided on the inner flange of the external ring 2 and on the facing flange of the inner ring 4.

The chain is protected by a coating (for example a silicone coating) and by a flexible sleeve (for example in Dacron®), such sleeve being fixed to the mitral annulus using standard surgical technique.

In another embodiment, which is not shown, the inner ring may be a spring. In a specific embodiment, the spring has a square spring having a quadrangular or rectangular cross-section. Inside the spring there is a metallic band that is free to move. With respect to round spiral spring, the square spiral spring allows the inner band to change its shape under the action of pressure if the pressure is applied to the thicker part of the band, but not if the pressure is applied to the thinner part of the band. This feature results in a mitral annulus that is easy deformed in one direction which is parallel to the valve plan but not in another direction, which is perpendicular to the valve plan.

The annuloplasty ring 1 is implanted with standard surgical technique currently used for mitral rings, by suturing the inner ring 4 to the valve annulus. The suture lines run only over the inner ring 4. The inner ring 4 is adjusted at best. The annuloplasty ring 1 is available in different sizes.

After the implantation of the ring 1, a specialized doctor, can change the geometry of the inner adjustable ring 4 for instance by using the actuating device and manually scrolling the cable 18 positioned under the skin under local anesthesia.

When the actuating device is activated, the pushing element 6 slides on the external ring 2 while pushing and pressing on the inner ring 4. When the pushing element 6 slides between the external rigid ring 2 and the inner deformable ring 4, the external ring 2 provides a support to the pushing element 6 in such a way that the pushing element 6 pushes on presses on the inner deformable ring 4, resulting in the changes in the shape of the inner ring 4, and therefore of the mitral annulus to which it is attached.

Therefore, a precise part of the inner ring 4 is deformed without modifying the perimeter of the inner ring 4, such part of the inner ring 4 deforming a precise corresponding part of the mitral valve. This movement reduces the distance between the anterior and the posterior leaflets of the mitral valve improving valve coaptation. The mitral valve can then be reshaped and repaired. Moreover, since the perimeter of the inner ring 4 is not reduced, the risk of stenosis is low.

With the ring 1, the action of reshaping the mitral annulus is local and doesn't affect the entire annulus. Using the surgical classification of the mitral valve anatomy that identifies three parts of the posterior leaflet of the mitral valve called P1, P2 and P3, the pushing element 6 is able to reshape the mitral annulus in P1 or P2 or P3 according to the need of the patient. As an example, when the pushing element 6 pushes P2, the posterior leaflet of the mitral valve approaches the anterior leaflet increasing leaflets' coaptation and valve continence.

The pushing element 6 can be pushed backward and forward as many times as necessary to find the optimal functioning of the valve.

More specifically, the doctor can reshape the mitral annuloplasty and verify the hemodynamic result in real time using standard echocardiography. If the ring 1 is still not correctly adjusted, the doctor can move again the pushing element 6 and find the best position. The doctor can adjust the form of the mitral ring 1 during the operation, on arrested heart, on beating heart and even after the operation has been completed, on a beating heart. Such adjustments could be done any time after the surgical procedure and could be repeated as much as needed. The adjustments could be made during, or just after the surgical procedure or a long time after such a surgical procedure, for example in the case of a morphologic modification of the valve.

The FIGS. 4 to 8 concern a preferred embodiment of the actuating device according to the invention. The actuating device 5 comprises transmission means linked with one end to the mechanical adjustment element and able to move the mechanical adjustment element when said transmission means are actuated. The transmission means comprise at least one cable 18.

Figure 4:
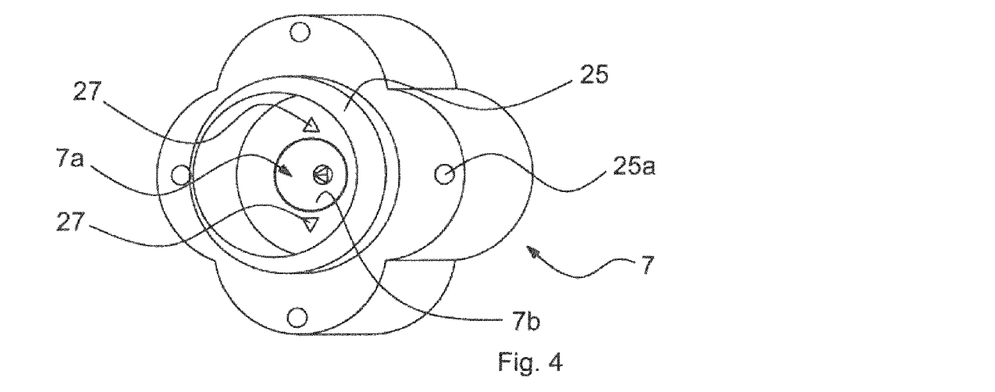
FIG. 4 shows, in a perspective view, an embodiment of a connecting means of the actuating device according to the invention.
Figure 5:
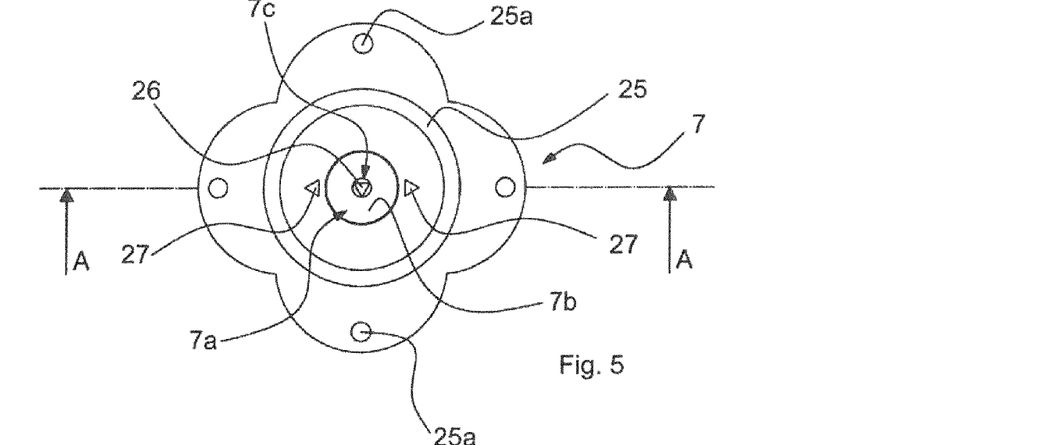
FIG. 5 shows, in a front view, the connecting means of the actuating device of FIG. 4.

The actuating device comprises also a connecting means 7, shown for instance in FIG. 4 and in FIG. 5, mounted on the other end of the transmission means and able to actuate the transmission means, said connecting means 7 comprising coupling means.

Two connecting means 7 may be used if two cables 18 are used for the pushing element displacement backward and/or forward, one pulley being connected to one cable. In other embodiments, only one connecting means may be used, such connecting means comprising only one pulley to which both cables are connected. Turning the pulley left or right will make the pushing element travel to the left or to the right.

Figure 6:
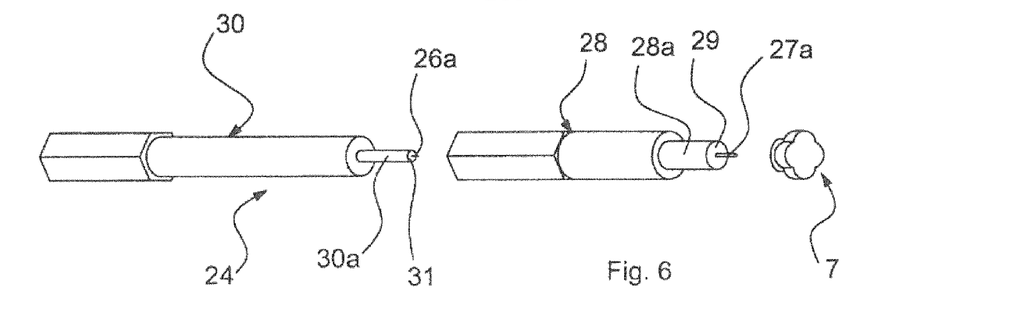
FIG. 6 shows, in an exploded view, an embodiment of some constitutive elements of a manually operated actuating device according to the invention.

The actuating device comprises also driving means 24, shown in FIG. 6, comprising complementary shaped coupling means. The driving means 24 are designed to be removable and to fit into the coupling means for moving the mechanical adjustment element by driving into movement a movable part of the connecting means 7.

Figure 9:
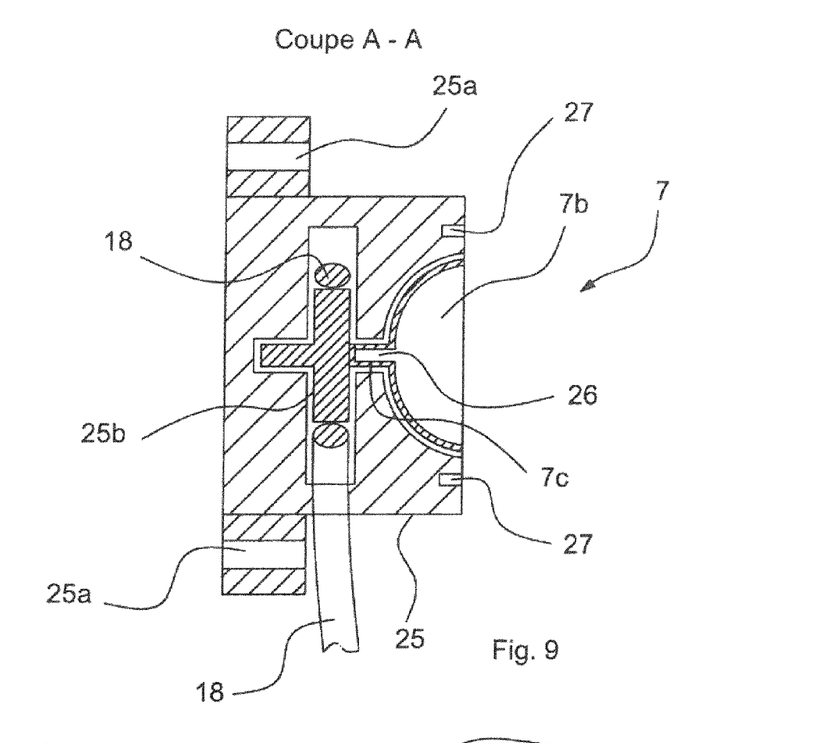
FIG. 9 shows a schematic and sectional view A-A of the connecting means of FIG. 5.

The connecting means 7 shown for instance in FIG. 9, on a sectional view, comprise a housing frame 25 which includes a pulley 25*b* for winding up and/or unwinding the cable 18. The movement of the cable 18 sets into movement the mechanical adjustment element when said pulley 25*b* is driven into rotation.

The movable part of the connecting means 7 comprises a rotating connecting element 7*a* which is mounted in the housing frame 25 and which turns with the pulley 25*b*.

The connecting means 7 further comprises locking means designed to lock the connecting means when the mechanical adjustment element has been moved in a best position. More specifically, the movable part of the connecting means 7 may comprise locking means designed to stop the rotation of the pulley when the pushing element has been moved in its best position.

The coupling means are designed to set into rotation the rotating connecting element 7*a* with respect of the housing frame 25.

According to an embodiment of the invention, the coupling means comprise a polygonal shaped connecting hole 26 in the center of the rotating connecting element 7*a* and at least two additional connecting holes 27 in the housing frame 25 on opposite locations with respect of the polygonal shaped connecting hole 26.

The rotating connecting element 7*a* presents an opened access on its top and a conical shaped gap 7*b* with a bottom 7*c* in which is machined the polygonal shaped connecting hole 26. The bottom 7*c* comprises a magnetic material in a preferred embodiment according to the invention. The conical shaped gap 7*b* may be filled with a malleable gel.

A covering space, delineated by a peripheral wall of the housing frame 25, may also be filled with the malleable gel, so that the polygonal shaped hole 26 and the additional connecting holes 27 are covered with the gel.

According to an embodiment of the invention, the housing frame 25 comprises attaching holes 25*a*, which may be used to attach the connecting means to the patient's ribs.

The complementary shaped coupling means of the driving means 24 comprise a centered polygonal shaped pin 26*a* and at least two additional pins 27*a* on opposite locations with respect of the polygonal shaped pin 26*a*. The driving means 24 are designed to set into a relative rotation the polygonal shaped pin 26*a* and the additional pins 27*a*.

The driving means 24 are designed to be manually activated like a manual tool and comprise a substantially cylindrical hollow tool part 28 presenting an annular edge 29 on which the additional pins 27*a* are protruding.

The driving means 24 comprise also an actuating tool part 30 which is sliding and rotating in the hollow tool part 28 and which has a crossing end 31 comprising the polygonal shaped pin 26*a*, said crossing end 31 being protruding from the annular edge 29.

The hollow tool part 28 as well as the actuating tool part 30 may comprise cylindrical end portions 28*a* and 30*a* with specific diameters, in order to fit with the size of the connecting means 7 and the coupling means.

In another configuration of the actuating device according to the invention, the external surface of the connecting means 7, shown for instance in FIG. 1*a*, is covered with a silicon or polymeric element, such as a foil or layer, in order to prevent direct contact between human tissue and the actuating device. This external protection allows however, the passage of the polygonal shaped pin 26*a* and of the additional pins 27*a*. The silicon or polymeric element is advantageously made of a self-sealing material.

Figure 7:
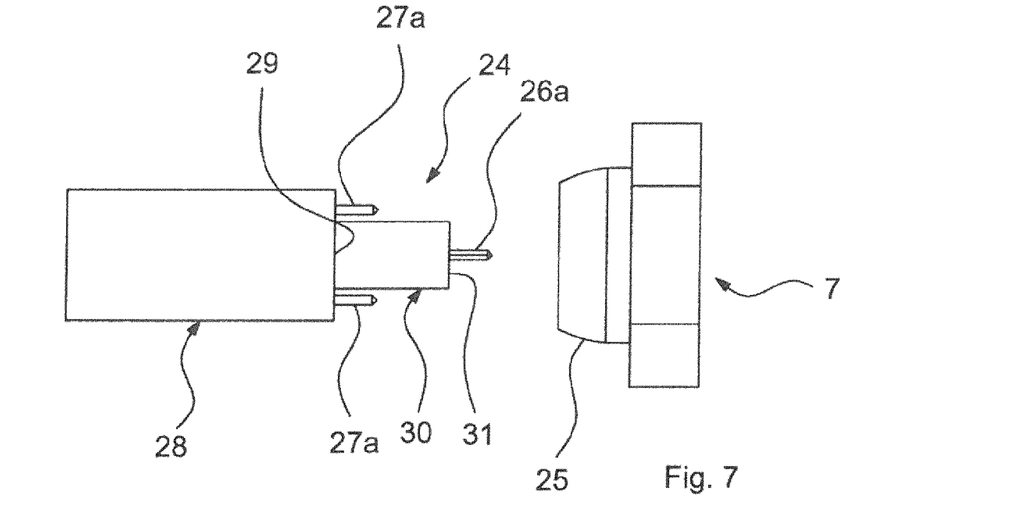
FIG. 7 shows an enlarged side view of a detail of the actuating device according to the invention.
Figure 8:
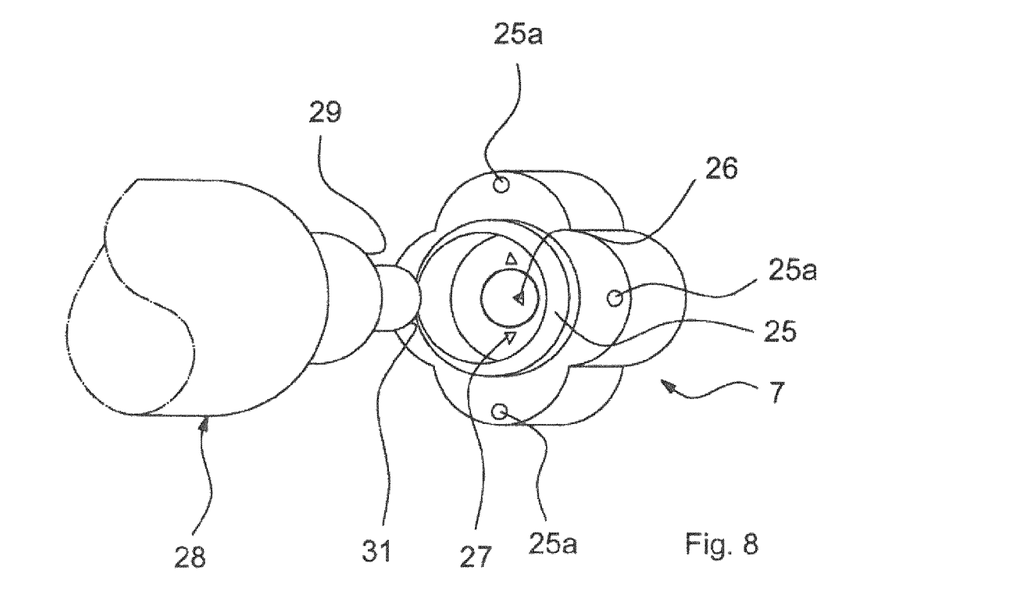
FIG. 8 shows an enlarged perspective view of a detail of the actuating device according to the invention.

FIG. 7 and FIG. 8, show respectively an enlarged side view and a perspective view of a detail of a detail of the actuating device according to the invention and more precisely of the driving means 24 and of the connecting means 7.

In an embodiment according to the invention, the additional connecting holes 27 and the additional pins 27*a* may also have a polygonal shape.

When the surgeon wants to move for instance the pushing element 6, he engages the actuating tool part 30 trough the hollow tool part 28 and through the malleable gel, until coupling the polygonal shaped pin 26*a* with the polygonal shaped hole 26 of the rotating connecting element 7*a*. The polygonal shaped pin 26*a* is first guided by the conical gap 7*b* and secondly secured in its final coupling position with the help of the magnetic bottom 7*c*.

In a next step, he introduces the extremity of the hollow tool part 28 in the housing frame 25, through the patient's skin and through the malleable gel so as to engage the additional pins 27*a* in the additional connecting holes 27.

In a next step, the surgeon can rotate manually the actuating tool part 30 with one hand, while keeping in a fixed position the hollow tool part 28 with its other hand. The actuating tool part 30 is used like a screw driver while holding the actuating device in place with the hollow tool part 28, called also outer tube.

Advantageously, the manually operated actuating device is designed to allow a bidirectional movement of the mechanical adjustment element.

According to another embodiment, illustrated for instance in FIG. 1, the driving means 24 comprise the removable control unit/actuator 8 attached to with the housing frame 25 and subcutaneous electrical contacts 20 connected with the control unit/actuator 8, said electrical contacts 20 being designed for providing a connection to a source of energy.

The control unit/actuator 8 comprises for instance an electric motor and the complementary shaped coupling means comprising a motor head on which the polygonal shaped pin 26*a* is attached to the rotor and on which the additional pins 27*a* are attached to the stator. The driving into rotation of the rotor is then used to move the mechanical adjustment element.

Some of the different manually operated steps of the surgeon, while moving the mechanical element can so be carried out by the control unit/actuator 8.

Figures 10, 11:
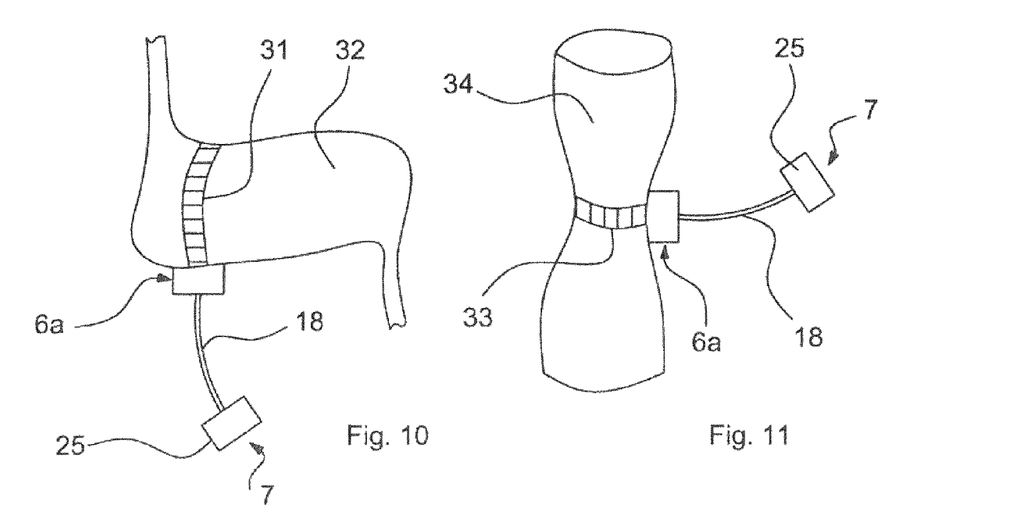
FIG. 10 shows a schematic view of an embodiment of a gastric banding device connected to an actuating device according to the present invention.
FIG. 11 shows a schematic view of an embodiment of an artery banding device connected to an actuating device according to the present invention.

FIG. 10 illustrates another example of application for the actuating device according to the invention. In this application, the surgical implant is a gastric band 31 placed around a stomach 32. The mechanical adjustment element is able to modify the diameter of the gastric band 31, resulting in a local tightening of the stomach 32. The mechanical adjustment element comprises for instance any means for actuating the gastric band 31, which is build like a gear type hose clamp 6*a* or like a worm-drive clamp.

FIG. 11 illustrates another example of application for the actuating device according to the invention. This application concerns artery banding in congenital cardiopathy. In this application, the surgical implant is an artery band 33 placed around a pulmonary artery 34. The mechanical adjustment element is able to reduce the diameter of the artery band 33, resulting in a tightening of the pulmonary artery 34. The mechanical adjustment element comprises for instance any means for actuating the artery band 34, which is build like a gear type hose clamp 6a or like a worm-drive clamp.

Naturally, the present invention can be subjected to numerous variations as to its implementation. Although several embodiments and implementations are described above, it should be understood that it is not conceivable to identify exhaustively all possible variants. It is naturally possible to envisage replacing any of the means described or any of the steps described with equivalent means or an equivalent step without going beyond the scope of the present invention.

The invention claimed is:

1. An actuating device for actuating a mechanical adjustment element of a surgical implant, said mechanical adjustment element allowing to modify at least one of a functional shape and a functional size of the surgical implant when actuated, wherein said actuating device comprises:
   transmission means in the form of a cable or a hydraulic, configured to be linked with one end to the mechanical adjustment element and able to move the mechanical adjustment element when said transmission means is actuated,
   connecting means mounted on the other end of the transmission means and able to actuate the transmission means, said connecting means comprising coupling means, and
   driving means comprising complementary shaped coupling means, said driving means being designed to be removable and fitted into the coupling means of the connecting means for moving the mechanical adjustment element by driving into movement a movable part of the connecting means,
   wherein the transmission means comprise at least one cable configured to link the mechanical adjustment element to the connecting means,
   the connecting means comprise a housing frame which includes a pulley for at least one of selected winding up and unwinding the cable and setting the mechanical adjustment element into movement when said pulley is driven into rotation, and
   the coupling means comprise a polygonal shaped connecting hole in a center of a rotating connecting element and at least two additional connecting holes in the housing frame on opposite locations with respect of the polygonal shaped connecting hole, said complementary shaped coupling means comprising a polygonal shaped pin and at least two additional pins on opposite locations with respect of the polygonal shaped pin, and said driving means being designed to set into a relative rotation in the polygonal shaped in and the additional pins.

2. The actuating device according to claim 1 wherein the rotating connecting element is mounted on the housing frame and is fixed to the pulley and which turns with the pulley.

3. The actuating device according to claim 2, wherein the coupling means are designed to set into rotation the rotating connecting element with respect of the housing frame.

4. The actuating device according to claim 3, wherein the surgical implant is an annuloplasty ring for repairing an atrioventricular cardiac valve, and said mechanical adjustment element is a sliding pushing element.

5. The actuating device according to claim 4, wherein the annuloplasty ring comprises an external support ring, an inner adjustable ring, the sliding pushing element being mounted between external and inner rings, said pushing element being designed to slide, when actuated, between the external ring and the inner ring by using the external ring as a support to push the inner ring locally in such a way that a precise part of the inner ring is deformed without modifying the perimeter of said inner ring.

6. The actuating device according to claim 3, wherein the surgical implant is a gastric band placed around a stomach, said mechanical adjustment element being able to modify a diameter of the gastric band, resulting in a local tightening of the stomach.

7. The actuating device according to claim 3, wherein the surgical implant is an artery band placed around a pulmonary artery, said mechanical adjustment element being able to reduce a diameter of the artery band, resulting in a tightening of the pulmonary artery.

8. The actuating device according to claim 1 wherein the rotating connecting element presents an opened access on its top and a conical shaped gap with a bottom in which is machined the polygonal shaped hole.

9. The actuating device according to claim 8, wherein the bottom comprises a magnetic material.

10. The actuating device according to claim 1 wherein the driving means are designed to be manually activated and comprise a substantially cylindrical hollow tool part presenting an annular edge on which the additional connecting pins are protruding and an actuating tool part which is sliding and rotating in the hollow tool part and which has a crossing end comprising the polygonal shaped pin, and said crossing end protruding from the annular edge.

11. The actuating device according to claim 1, wherein the actuating device is designed to allow a bidirectional movement of the mechanical adjustment element.

12. The actuating device according to claim 1, wherein the connecting means further comprises locking means designed to stop rotation of the pulley and lock the connecting means when the mechanical adjustment element has been moved in a best position.

13. A surgical implant comprising a mechanical adjustment element, said mechanical adjustment element being able to modify at least on of a functional shape and a functional size of the surgical implant when actuated, wherein the surgical implant comprises an actuating device in accordance with claim 1.

* * * * *